(12) United States Patent
Heindl et al.

(10) Patent No.: US 9,796,746 B2
(45) Date of Patent: Oct. 24, 2017

(54) COMPOUNDS USEFUL FOR FRET AND METHODS RELATED THERETO

(71) Applicant: Roche Diagnostics Operations, Inc., Indianapolis, IN (US)

(72) Inventors: Dieter Heindl, Munich (DE); Joachim Hoenes, Zwingenberg (DE); Carina Horn, Biblis (DE); Thomas Meier, Munich (DE); Wolfgang Petrich, Bad Schoenborn (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/959,280

(22) Filed: Dec. 4, 2015

(65) Prior Publication Data

US 2016/0090398 A1 Mar. 31, 2016

Related U.S. Application Data

(63) Continuation of application No. PCT/EP2014/061589, filed on Jun. 4, 2014.

(30) Foreign Application Priority Data

Jun. 4, 2013 (EP) .................................. 13002864

(51) Int. Cl.
| | |
|---|---|
| *C07H 19/207* | (2006.01) |
| *G01N 33/533* | (2006.01) |
| *G01N 33/535* | (2006.01) |
| *G01N 33/542* | (2006.01) |
| *G01N 33/573* | (2006.01) |
| *G01N 33/58* | (2006.01) |
| *C12Q 1/26* | (2006.01) |
| *G01N 21/64* | (2006.01) |

(52) U.S. Cl.
CPC ............. *C07H 19/207* (2013.01); *C12Q 1/26* (2013.01); *G01N 21/6428* (2013.01); *G01N 33/533* (2013.01); *G01N 33/535* (2013.01); *G01N 33/542* (2013.01); *G01N 33/5735* (2013.01); *G01N 33/581* (2013.01); *G01N 33/582* (2013.01); *G01N 2201/062* (2013.01); *G01N 2333/90248* (2013.01)

(58) Field of Classification Search
CPC .................................................... G01N 33/533
See application file for complete search history.

(56) References Cited

U.S. PATENT DOCUMENTS

| 4,446,231 A | 5/1984 | Self |
| 4,735,897 A | 4/1988 | Vary et al. |
| 2005/0214891 A1 | 9/2005 | Horn et al. |
| 2006/0003397 A1 | 1/2006 | Knappe et al. |

FOREIGN PATENT DOCUMENTS

| EP | 0293732 A2 | 12/1988 |
| WO | 2007/012494 A1 | 2/2007 |
| WO | 2010/094632 A1 | 8/2010 |
| WO | 2011/012270 A1 | 2/2011 |

OTHER PUBLICATIONS

Akshath, Uchangi Satyaprasad., Quantum dots as nano plug-in's for efficient NADH resonance energy routing, Biosensors and Bioelectornics, 2012, pp. 411-415, vol. 38.
Anderson, Bruce M., Analogs of Pyridine Nucleotide Coenzymes, The Pyridine Nucleotide Coenzymes, 1982, pp. 91-133, Ch. 4.
Bahshi, Lily et al., Optical Detection of Glucose by Means of Metal Nanoparticles or Semiconductor Quantum Dots, Small, 2009, pp. 676-680, vol. 5, No. 6.
Fjeld, Clark C. et al., Differential binding of NAD+ and NADH allows the transcriptional corepressor carboxyl-terminal binding protein to serve as a metabolic sensor, Proceedings of the National Academy of Sciences USA, 2003, pp. 9202-9207, vol. 100, No. 16.
International Search Report issued Aug. 4, 2014, in Application No. PCT/EP2014/061589, 6 pages.
Li, Mengying et al., Hydrothermal synthesis of highly luminescent CdTe quantum dots by adjusting precursors' concentration and their conjunction with BSA as biological fluorescent probes, Talanta, 2007, pp. 89-94, vol. 72.
Lindberg, Margareta et al., A New Immobilized NAD+ Analogue, Its Application in Affinity Chromatography and as a Functioning Coenzyme, European Journal of Biochemistry, 1973, pp. 187-193, vol. 40.
Liu, Minghui et al., A DNA tweezer-actuated enzyme nanoreactor, Nature Communications, 2013, 5 pages, vol. 4.
Oppenheimer, Norman J., Chemistry and Solution Conformation of the Pyridine Coenzymes, The Pyridine Nucleotide Coenzymes, 1982, pp. 51-89, Ch. 3, Academic Press, Inc., New York.
Von Ketteler, Alexa et al., Fluorescence Properties of Carba Nicotinamide Adenine Dinucleotide for Glucose Sensing, ChemPhysChem, 2012, pp. 1302-1306, vol. 13.
Wolff, Edith C. et al., Deoxyhypusine Synthase Generates and Uses Bound NADH in a Transient Hydride Transfer Mechanism, The Journal of Biological Chemistry, 2000, pp. 9170-9177, vol. 276, No. 13.

*Primary Examiner* — Bin Shen
(74) *Attorney, Agent, or Firm* — Roche Diagnostics Operations, Inc.

(57) ABSTRACT

The invention also relates to compounds, which are useful for intra-molecular fluorescence resonance energy transfer (FRET), comprising the oxidized form of a carbaNADH-based first fluorophore and a second fluorophore that is excitable at a wave-length of between 445 to 540 nm and that has an emission maximum of greater than 560 nm, and methods, kits and compositions related thereto.

9 Claims, 3 Drawing Sheets

COMPOUNDS USEFUL FOR FRET AND METHODS RELATED THERETO

This application claims priority to PCT/EP2014/061589 which was filed on Jun. 4, 2014 which claims priority to European Application 13003864.0 which was filed on Jun. 4, 2013. This reference is incorporated by reference herein in its entirety. The invention also relates to compounds, which are useful for intra-molecular fluorescence resonance energy transfer (FRET), comprising the oxidized form of a carbaNADH-based first fluorophore and a second fluorophore that is excitable at a wave-length of between about 445 to about 540 nm and that has an emission maximum of greater than about 560 nm, and methods, kits and compositions related thereto.

BACKGROUND

Many bioanalytical methods are based on the oxidative status of nicotinamide adenine dinucleotide (NAD) or nicotinamide adenine dinucleotide phosphate (NADP). NAD has a multiple ringed structure, which undergoes redox reactions within its nicotinamide ring. The closely related NADP molecule is phosphorylated on the 2' position of the adenosine ribose ring.

NAD and NADP can be reversibly reduced by the formal addition of hydride ions and both molecules act as coenzymes in reversible reactions. Accordingly, enzymatic reactions based on NAD and NADH are amenable to fluorescent analysis.

Many oxidoreductase enzymes can use these cofactors to transfer hydrogen groups between molecules. Because the reduced forms of these molecules differ from their oxidized forms in their ability to absorb light, reactions have been quantitated based on light absorption at 340 nm or by fluorescent emission of light at 445 nm.

Enzymatic dehydrogenase reactions can take advantage of the property of the reduced forms of NAD and NADP to absorb light at a wavelength of 340 nm while the oxidized form does not. Similarly, the reduced forms are capable of fluorescent emission at 445 nm when excited at 340 nm, while the oxidized forms are not. These properties permit quantitation of reactions that directly involve a change in the oxidative state of these cofactors. For example, when phosphoglycerate kinase and glyceraldehyde-3-phosphate dehydrogenase are used to catalyze the formation of NAD from NADH in the presence of adenosine triphospate (ATP), the concentration of adenosine triphosphate can be measured as a decrease in fluorescence intensity (U.S. Pat. Nos. 4,446,231 and 4,735,897).

Oxidoreductases are also quite popular in the quantitative measurement of blood glucose levels, see for example EP 0 293 732A2, US 2005/0214891 A1, and US 2006/0003397. All of these publications describe a similar test protocol for measurement of glucose, in which a reagent system containing the enzyme-coenzyme pair glucose dehydrogenase (GlucDH)/nicotinamide adenine dinucleotide (NAD) is used. Upon action of GlucDH, a hydride ion is transferred from glucose to NAD, such that NADH forms. The resulting quantity of NADH is directly correlated to the concentration of glucose. NADH is a strong fluorophore, whose concentration can be determined by a measurement of the fluorescence intensity. Analyte concentration in a sample is typically determined by correlating the fluorescence intensity measured to a calibration curve obtained with known analyte concentrations.

Evidently, enzyme-based measuring systems for biochemical analytics are important components of clinically relevant analytical methods. This primarily concerns the measurement of analytes e.g. metabolites or substrates which are determined directly or indirectly with the aid of an enzyme. The analytes are converted with the aid of an enzyme-coenzyme complex and subsequently quantified. In this process the analyte to be determined is brought into contact with a suitable enzyme and a coenzyme where the enzyme is usually used in catalytic amounts. The coenzyme is changed e.g. oxidized or reduced by the enzymatic reaction. This process can e.g. be detected photo metrically. A calibration provides a direct correlation between the measured value and the concentration of the analyte to be determined.

Coenzymes are organic molecules which are covalently or non-covalently bound to an enzyme and are changed by the conversion of the analyte. Prominent examples of coenzymes are nicotinamide adenine dinucleotide (NAD) and nicotinamide adenine dinucleotide phosphate (NADP) from which NADH and NADPH respectively are formed by reduction.

Many oxidoreductase-based measuring systems known from the prior art have a limited shelf-life and require cautious handling such as cooling or dry storage in order to achieve sufficient storage life. Erroneous results caused by incorrect, unnoticed, faulty storage can therefore occur. In particular the exhaustion of desiccants due to opening of the primary packaging and long-time use periods can result in measuring errors.

Both the essential components of such enzyme-based measurement systems, i.e. the enzyme the coenzyme can independently contribute to such limited stability. For example coenzymes such as NAD and NADP are known to be rather unstable.

Both NAD and NADP are base-labile molecules the degradation paths of which are described in the literature (see e.g. N. J. Oppenheimer in The Pyridine Nucleotide Coenzymes Academic Press, New York, London 1982, J. Everese, B. Anderson, K. Yon, Editors, chapter 3, pages 56-65). Essentially ADP-ribose is formed during the degradation of NAD or NADP by cleavage of the glycosyl bonds between the ribose and the pyridine unit. The reduced forms NADH and NADPH are acid labile; e.g. epimerization is a known degradation path.

The instability of NAD/NADP and of NADH/NADPH is due to the lability of the glycosyl bond between the ribose and the pyridine unit. But even under conditions that are not drastic such as in aqueous solution, the coenzymes NAD and NADP may already be hydrolysed solely due to ambient humidity.

CarbaNAD is an analogue to NAD, wherein ribose is substituted by a carbacyclic sugar unit. CarbaNAD (or Carba-NAD) has the following structure (I):

However, even when using the more stable coenzyme carbaNAD, an array of quite fundamental problems is connected to the measurement of fluorescence intensity including the following:

One important source of errors for measurements based on fluorescence intensity measurements comes from non-specific light, which reaches the detector from the environment and can cause an unspecific signal.

The intensity of the measured fluorescence light is not only a function of the quantity of the fluorophore. Rather it is also significantly influenced by its molecular environment in the sample. In particular processes which are summarized under the term fluorescence quenching contribute errors in measurements.

The position and orientation of the molecule can change between absorption and emission because in the statistical mean a time in the order of nanoseconds passes between the excitation of a molecule and the emission of a light quantum. Interfering influences result therefrom in regard to the fluorescence intensity, in particular temperature dependence.

Fluorescence is generally excited by ultraviolet light. Photochemical reactions of the electronically excited state may cause bleaching of the fluorophore. This is a further error source.

On this basis, it is an object of the present invention to propose a method which allows for an improved measurement in particular in regard to the described stability issues, measurement errors and interferences.

SUMMARY OF THE INVENTION

The present invention relates to a compound comprising
(1) the oxidized form of a carbaNADH-based first fluorophore and
(2) a second fluorophore that is excitable with light having a wave-length of between 445 to 540 nm and that has an emission maximum auf greater than 560 nm,
particularly wherein the carbaNADH-based first fluorophore and the second fluorophore are covalently linked.

In another embodiment, the present invention relates to a fluorescence-based method for determining the concentration or amount of an analyte in a sample.

BRIEF DESCRIPTION OF THE DRAWINGS

FIG. 3 shows the structure (FIG. 3A) as well as the extinction spectrum (FIG. 3B) and emission spectrum (FIG. 3C) of oxacarbocyanine (C3) dye.

DETAILED DESCRIPTION

The present invention relates to a compound comprising:
(1) the oxidized form of a carbaNADH-based first fluorophore and
(2) a second fluorophore that is excitable with light having a wave-length of between 445 to 540 nm and that has an emission maximum auf greater than 560 nm.
particularly wherein the carbaNADH-based first fluorophore and the second fluorophore are covalently linked.

The compound of the invention is particulary useful in intra-molecular fluorescence resonance energy transfer (FRET) methods, e.g. as detailed in the present description.

In an embodiment, the emission maximum of the second fluorophore is between 560 and 750 nm.

In another embodiment, the second fluorophore is excitable with light having a wave-length of between 445 to 475 nm.

In some embodiments, the carbaNADH-based first fluorophore is excitable with light having a wavelength of between 300 to 400 nm, preferably 360 to 380 nm, more preferably 365 to 385 nm, most preferably 370 to 380 nm.

CarbaNADH is maximally excitable with light having a wavelength of 360 nm.

The emission maximum of carbaNADH is 465 nm.

Figure 2:
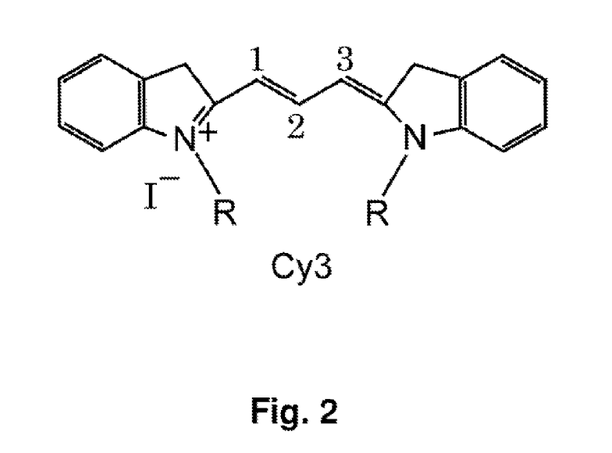
FIG. 2 shows the chemical structure of Cy3 as known in the art. The designation Cy3 relates to number of the methines (as shown), and the side chains were unspecified. Thus various structures are designated Cy3 in the literature. The R groups do not have to be identical. In the dyes as commonly used, they are short aliphatic chains one or both of which ends in a highly reactive moieties such as N-hydroxysuccinimide or maleimide.

Using such compound for FRET overcomes the above-described deficiencies of NAD-derived compounds in fluorescence-based methods. As described in the Examples, the compound N6-[N-(6-"Cy3" aminohexyl)carbamoylmethyl] carbaNADH is proven to be useful for FRET methods. "Cy3" defines a class of compounds as shown in FIG. 2 and is also referred to as a 2-[3-[1-(hexan-5-oyl)-1,3-dihydro-3, 3-dimethyl-5-sulfo-2H-indol-2-ylidene]-1-propen-1-yl]-3, 3-dimethyl-5-sulfo-1-(3-sulfophenyl)-3H-Indolium entity, wherein the carbonyl group of the hexanoyl group is connected with the aminogroup of the aminohexyl group).

The term "carbaNADH-based first fluorophore" is used to indicate that only the reduced form of a compound based on the carbaNAD/carbaNADH redox-system which fluoresces between 400 and 570 nm The enzymatic substrate is usually a compound or fluorogenic coenzyme according to the present invention in its oxidized (carbaNAD) form (also referred to as the oxidized form of a carbaNADH-based first fluorophore).

A compound according to the present invention, comprises a carbaNAD moiety, and thus a nicotinamide entity and an adenosine entitity, respectively. The nicotinamide entity can be reduced to an 1,4 dihydronicotinamide entity, which acts as the fluorophore. The nicotinamide entity is always unsubstituted. The remaining atoms of the adenosine entity may be substituted. As obvious to the skilled artisan such substitution must compatible with the enzymatic reaction of interest. Such substitutions are listed in The pyridine nucleotide coenzymes. New York, N.Y.: Academic Press Inc.; 1982. Chapter 4: B. M. Anderson Analogs of Pyridine Nucleotide Coenzmes pp. 91-134. One common substituent is a phosphate group on the 2' OH group of the adenosine entity, resulting in a CarbaNADP moiety. Preferably, substituents are on the adenine nucleobase (The pyridine nucleotide coenzymes. New York, N.Y.: Academic Press Inc.; 1982. Chapter 4: B. M. Anderson Analogs of Pyridine Nucleotide Coenzmes pp. 103-104 table I Item II A). Most preferred positions for substitutions are N6 and C8 of the adenine nucleobase. Suitable substituent groups at N6 and C8 independently are $C_1$ to $C_{12}$ alkyl, alkenyl or alkinyl groups, which are optionally interrupted by one or more O, N and/or S atoms, and wherein said $C_1$ to $C_{12}$ alkyl , alkenyl or alkinyl groups are optionally substituted with =O, —OH, —SH, =S, or $C_1$ to $C_4$ alkyl, which alkyl is optionally substituted or interrupted by one or more O, N or S atoms, and wherein preferably one of N6 or C8 is connected via a linker molecule with a length of 25 atoms or less to the second fluorophore. A carbaNAD-based moiety is understood as carbaNAD moiety, which is optionally substituted as defined above.

The oxidized form of carbaNADH, namely carbaNAD, has the structure of formula (I) above.

In a preferred ambodiment, the oxidized form of the carbaNADH-based first fluorophore is a carbaNADH-based first fluorophore of formula II (II)

wherein

Q is a $NR_1R_2$, wherein $R_1$ and $R_2$ are independently selected from H, a $C_1$ to $C_{12}$ alkyl group, a $C_1$ to $C_{12}$ alkenyl group and a $C_1$ to $C_{12}$ alkinyl group, optionally wherein one or more carbon atoms of the alkyl group, a alkenyl group and a alkinyl group is substituted with O, N or S and/or optionally wherein said $C_1$ to $C_{12}$ alkyl, alkenyl or alkinyl group is substituted with =O, —OH, —SH, =S or a $C_1$ to $C_4$ alkyl, wherein optionally one or more carbon atoms of the alkyl group is substituted with O, N or S, and J is selected from H, a $C_1$ to $C_{12}$ alkyl group, a $C_1$ to $C_{12}$ alkenyl group and a $C_1$ to $C_{12}$ alkinyl group, optionally wherein one or more carbon atoms of the alkyl group, a alkenyl group and a alkinyl group is substituted with O, N or S and/or optionally wherein said $C_1$ to $C_{12}$ alkyl, alkenyl or alkinyl group is substituted with =O, —OH, —SH, =S or a $C_1$ to $C_4$ alkyl, wherein optionally one or more carbon atoms of the alkyl group is substituted with O, N or S, particularly wherein one of J and Q is connected via a linker molecule with a length of 25 atoms or less to the second fluorophore, and T is a hydrogen atom or phosphate group, especially wherein Q is substituted with N-(6"cy3" aminohexyl)carbomyolmethyl.

In a further preferred embodiment, the carbaNADH-based first fluorophore and the second fluorophore are covalently linked, e.g. as for N6-[N-(6-"Cy3" amino-hexyl)carbamoylmethyl] carbaNADH.

In a further preferred embodiment, the distance between the first and the second fluorophore is between 1.5 and 5 nm.

In a further preferred embodiment, the compound consists of
(i) a the oxidized form of a carbaNADH-based first fluorophore, and
(ii) a second fluorophore that is excitable with light having a wave-length of between 445 to 540 nm, and that has an emission maximum auf greater than 560 nm, and
(iii) a linker molecule with a length of 25 atoms or less.

In case of N6-[N-(6-"Cy3" aminohexyl) carbamoylmethyl] carbaNADH, the linker has the structure —$CH_2$-C(=O)NH—$(CH_2)_6$—NH—C(=O)$(CH_2)_5$—. This linker has a length of 16 atoms.

A "linker molecule with a length of X atoms" is understood as linker which has X atoms in the straight chain connecting the two other moieties (i) and (ii).

Preferred linkers are alkylene, alkenylene, or alkinylene entities, which are optionally interrupted by one or more O, N and/or S atoms, and wherein said alkylene, alkenylene, or alkinylene entities are optionally substituted with =O, —OH, —SH, =S, or, $C_1$ to $C_4$ alkyl groups, which alkyl group is optionally substituted or interrupted by one or more O, N or S atoms. In particular, linkers may comprise —O—$CH_2$—$CH_2$—O-moieties, amide groups and/or ether groups.

Preferably, a linker is connected to the N6 or C8 atom of the adenine moiety of the carbaNADH-based first fluorophore or the NADH-based first fluorophore defined below.

In a yet further preferred embodiment, the first fluorophore is carbaNADH. Therefore, in another preferred embodiment, the oxidized form of the first fluorophore is carbaNAD.

"The first fluorophore is carbaNADH" is understood as that the compound of the invention carries a carbaNADH moiety as first fluorophore.

A "fluorophore" according to the present invention is a moiety which is able to fluoresce at room temperature and in aqueous solution.

In a yet further preferred embodiment, the second fluorophore has an absorption of less than 5% of the maximal absorption for said second fluorophore at a wavelength of 360 nm. In a more preferred embodiment, the second fluorophore has an absorption of less than 3% of the maximal absorption for said second fluorophore at wavelength of 360 nm.

This ensures that no or only negligible unwanted direct excitation of the second fluorophore is obtained when the first fluorophore is excited.

Efficient energy transfer from the first fluorophore to the second fluorophore occurs when there is a spectral overlap of the first fluorophore emission spectrum and the second fluorophore excitation spectrum.

Figure 3A:
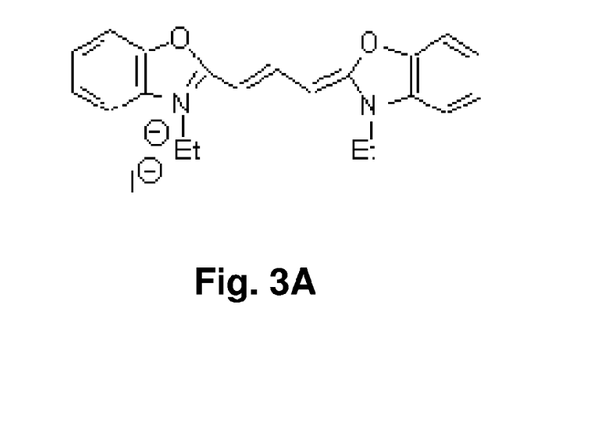
Figure 3B:
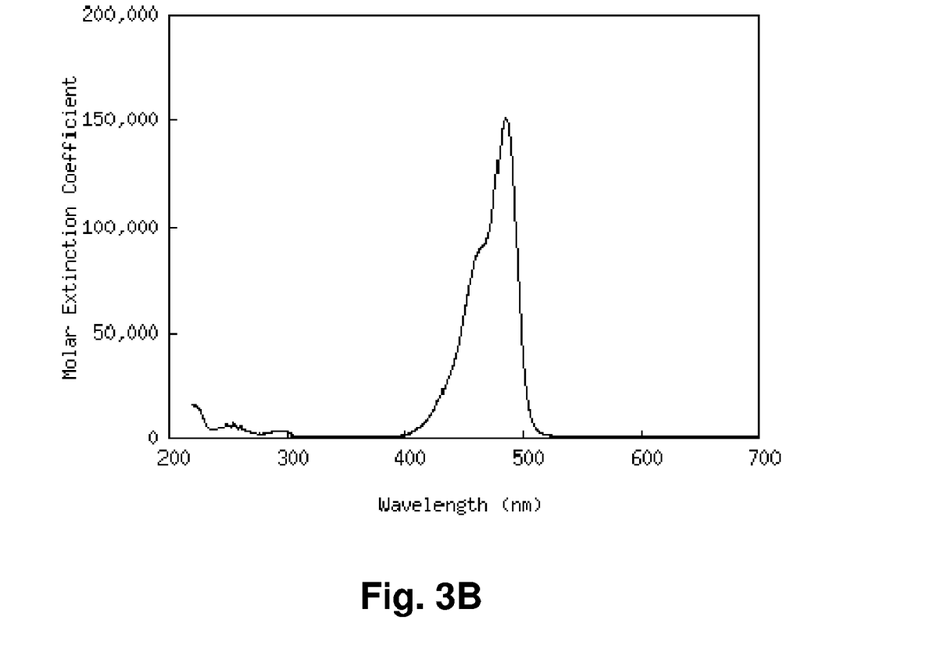
Figure 3C:
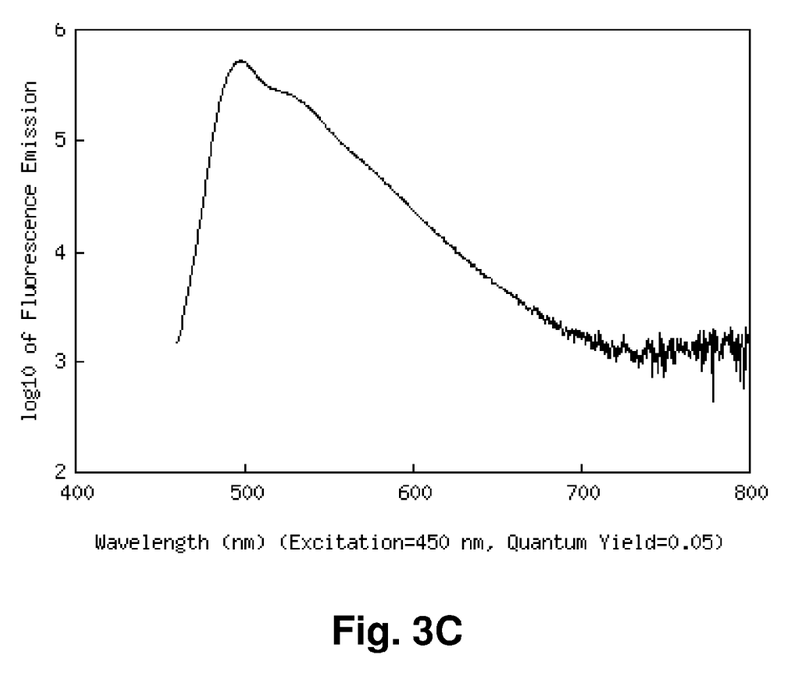

Examples for suitable second fluorophores in a compound of the present invention or in a fluorogenic coenzyme for use in a method according to the present invention are fluorophores comprising, as a core, chromophores selected from the group consisting of: a 2-[3-(1,3-dihydro-1,3,3-trimethyl-2H-indol-2-ylidene)-1-propen-1-yl]-1,3,3-trimethyl-3H-indolium-chromophore moiety (as in "Cy3"), a 5,6-dichloro-2-[3-(5,6-dichloro-1,3-dihydro-1,3-dimethyl-2H-benzimidazol-2-ylidene)-1-propen-1-yl]-1,3-dimethyl1H-benzimidazolium chromophore moiety, a 1-methyl-4-[3-(1-methyl-4(1H)-quinolinylidene)-1-propen-1-yl]-quinolinium chromophore moiety, (as in pynacynol), and a 2-(4-(Diethylamino)-2-hydroxyphenyl)-4-(4-(diethyliminio)-2-hydroxycyclohexa-2,5-dienylidene)-3-oxocyclobut-1-enolate chromophore moiety (a squarylium dye). These chromophores are referred to as core, since they may additionally comprise one or more substituents, wherein the substituents do not alter the basic structure of the substituted chromophore when compared to the unsubstituted chromophore. Particularly, the one or more substituents replace one or more hydrogen residues present in the unsubstituted chromophore. Typical substituents include, but are not limited to, short alkyl residues, such as methyl, ethyl or propyl, or alkoxy residues, such as methoxy, ethoxy or propoxy. Suitable chromophores are also shown in FIGS. 2 and 3.

A skilled person is able to select further suitable dyes by recording excitation and emission spectra of a given dye.

A preferred fluorophore comprises as a core the 2-[3-(1,3-dihydro-1,3,3-trimethyl-2H-indol-2-ylidene)-1-propen-1-yl]-1,3,3-trimethyl-3H-indolium-chromophore moiety (as in "Cy3") or a core as shown in FIG. 2.

N6-[N-(6-"Cy3" aminohexyl)carbamoylmethyl] carbaNAD and its reduced form are particularly preferred compounds of the invention, as shown by the Examples.

Using NADH-dependent oxidoreductases, the reduced form of the compounds can be recycled to the oxidized form. Therefore, the present invention also relates in a further aspect to the reduced form of a compound of the invention, and mixtures of the oxidized and reduced forms.

In a preferred embodiment, the reduced form of the carba a carbaNADH-based first fluorophore is a carbaNADH-based first fluorophore of formula III especially wherein Q is substituted with N-(6"cy3" aminohexyl)carbomyolmethyl.

In a preferred embodiment, the invention also relates to N6-[N-(6-"Cy 3" aminohexyl)carbamoylmethyl] carbaNADH, N6-[N-(6-"Cy 3" aminohexyl)carbamoylmethyl] carbaNAD, or a mixture of N6[N-(6-"Cy 3" aminohexyl) carbamoylmethyl] carbaNAD and N6-[N-(6-"Cy 3" aminohexyl)carbamoylmethyl] carbaNADH.

In a yet further embodiment, the present invention relates to a reagent system (also referred to as kit) comprising
(a) a compound useful for FRET of the invention, and
(b) an NAD(H)-dependent oxidoreductase.

Such reagent system or kit can be used in methods for determining an analyte in a sample.

The invention further relates to the use of a compound of the invention, or of a reagent system of the invention, or of a kit of the invention, for determining the amount and/or concentration of an analyte in a sample.

The invention further relates to the use of a compound useful for FRET of the invention, or of a reagent system of the invention, or of a kit of the invention, as FRET agent.

The invention further relates to a kit comprising
(a) a compound of the invention or a fluorogenic coenzyme as defined in the context of the methods of the invention,
(b) optionally an NAD(H)-dependent oxidoreductase, and
(c) optionally further reagents.

In a further embodiment, the present invention relates to a method for determining an analyte in a sample using an NAD(H)-dependent oxidoreductase and the oxidized form of a fluorogenic coenzyme, the method comprising following steps:

(III)

wherein
Q is a NR$_1$R$_2$, wherein R$_1$ and R$_2$ are independently selected from H, a C$_1$ to C$_{12}$ alkyl group, a C$_1$ to C$_{12}$ alkenyl group and a C$_1$ to C$_{12}$ alkinyl group, optionally wherein one or more carbon atoms of the alkyl group, a alkenyl group and a alkinyl group is substituted with O, N or S and/or optionally wherein said C$_1$ to C$_{12}$ alkyl, alkenyl or alkinyl group is substituted with =O, —OH, —SH, =S or a C$_1$ to C$_4$ alkyl, wherein optionally one or more carbon atoms of the alkyl group is substituted with O, N or S, and
J is selected from H, a C$_1$ to C$_{12}$ alkyl group, a C$_1$ to C$_{12}$ alkenyl group and a C$_1$ to C$_{12}$ alkinyl group, optionally wherein one or more carbon atoms of the alkyl group, a alkenyl group and a alkinyl group is substituted with O, N or S and/or optionally wherein said C$_1$ to C$_{12}$ alkyl, alkenyl or alkinyl group is substituted with =O, —OH, —SH, =S or a C$_1$ to C$_4$ alkyl, wherein optionally one or more carbon atoms of the alkyl group is substituted with O, N or S, particularly wherein one of J and Q is connected via a linker molecule with a length of 25 atoms or less to the second fluorophore, and T is a hydrogen atom or phosphate group, (a) mixing an NAD(H)-dependent oxidoreductase and the oxidized form of a fluorogenic coenzyme with the sample, thereby
(b) reacting the analyte with the reagent system comprising an NAD(H)-dependent oxidoreductase and the oxidized form of a fluorogenic coenzyme,
(c) measuring the fluorescence emission of the reduced coenzyme,
wherein the fluorogenic coenzyme is a compound comprising
(1) an NADH-based first fluorophore, and
(2) a second fluorophore that is excitable with light having a wave-length of between 445 to 540 nm, and that has an emission maximum auf greater than 560 nm.

In another preferred embodiment, the second fluorophore is excitable with light having a wave-length of between 445 to 475 nm.

"NADH-based fluorophore" is understood as fluorophore comprising a NADH-based moiety, or a carbaNADH-based moiety, respectively.

An oxidized form of a NADH-based moiety for use in method of the invention comprises an NAD moiety, which is optionally substituted. The corresponding reduced NADH-based moiety comprises a 1,4 dihydronicotinamide entity of NADH, which acts as the fluorophore, and which 1,4 dihydronicotinamide entity is always unsubstituted. The remaining atoms of the NADH moiety may be substituted. As obvious to the skilled artisan such substitution must compatible with the enzymatic reaction of interest. A preferred substituent is a phosphate group on the 2' OH group of the adenosine entity, resulting in a NADPH moiety. Preferred other positions for substitutions are N6 and C8 of the adenine nucleobase. Suitable substituent groups at N6 and C8 independently are $C_1$ to $C_{12}$ alkyl, alkenyl or alkinyl groups, which are optionally interrupted by one or more O, N and/or S atoms, and wherein said $C_1$ to $C_{12}$ alkyl, alkenyl or alkinyl groups are optionally substituted with =O, —OH, —SH, =S, or $C_1$ to $C_4$ alkyl which alkyl is optionally substituted or interrupted by one or more O, N or S atoms. More preferably, one of N6 or C8 of the adenine nucleobase is connected via a linker molecule with a length of 25 atoms or less to the second fluorophore.

In a further preferred embodiment, the fluorogenic coenzyme consists of
 (i) an NADH-based first fluorophore, and
 (ii) a second fluorophore that is excitable with light having a wave-length of between 445 to 540 nm, and that has an emission maximum auf greater than 560 nm, and
 (iii) a linker molecule with a length of 25 atoms or less.

Preferably, the NADH-based first fluorophore is excitable with light having a wave-length of between 300 to 400 nm, preferably 360 to 380 nm, more preferably 365 to 385 nm, most preferably 370 to 380 nm.

NADH is excitable with light having a wavelength of 340 nm.

carbaNADH is maximally excitable with light having a wavelength of 360 nm.

The emission maximum of both NADH and carbaNADH is 465 nm.

Both NADH and carbaNADH are suitable first fluorophores according to the present invention.

Therefore, in a preferred embodiment, the NADH-based first fluorophore is selected from the group consisting of NADH and carbaNADH. In a more preferred embodiment, the NADH-based fluorophore is selected from NADH, NADPH, carbaNADH and carbaNADPH, even more preferably from NADH and carbaNADH, most preferably carbaNADH.

In a further more preferred embodiment, the the oxidized form of the NADH-based fluorophore is selected from NAD, NADP, carbaNAD and carbaNADP, even more preferably from NAD and carbaNAD, most preferably carbaNAD. Such oxidized forms of the first fluorophores are present in the oxidized forms of the fluorogenic enzymes for use in methods of the invention.

In a preferred embodiment, the fluorogenic coenzyme and its oxidized form for use in a method according to the present invention is a compound of the invention described above.

Such compound useful for performing intra-molecular fluorescence resonance energy transfer (FRET) comprises:
 (1) the oxidized form of a carbaNADH-based first fluorophore and
 (2) a second fluorophore that is excitable with light having a wave-length of between 445 to 540 nm and that has an emission maximum auf greater than 560 nm.

The preferred embodiments described above for fluorophores comprising a NADH-based moiety or a carbaNADH-based moiety, respectively, also apply to the methods of the invention.

Preferably, the method of the invention is followed by determining the amount and/or concentration of the analyte based on the fluorescence emission of the fluorogenic coenzyme.

In a preferred embodiment of the method, a change in the oxidized form of the fluorogenic coenzyme is generated in step (b).

In a particularly preferred embodiment, said change in the oxidized form of the fluorogenic coenzyme is a reduction of the fluorogenic coenzyme.

In a further particularly preferred embodiment, said change in the coenzyme correlates with the amount and/or concentration of the analyte.

An analyte may for example be a metabolite or substrate which can be determined directly or indirectly with the aid of an NAD(H)-dependent oxidoreductase as enzyme. The analyte is reacted in the presence of the enzyme-coenzyme complex and can then be quantified. For this, the analyte to be determined is brought into contact with a suitable enzyme, and a coenzyme, wherein the coenzyme is reduced by the enzymatic reaction. A calibration provides the direct relationship of the measured value and the concentration of the analyte to be determined.

The analyte may be present in body fluids like blood, serum, plasma or urine, or in waste water or food. As analyte any biological or chemical compound may be determined, which can be analyzed by a NAD(H)-dependent oxidoreductase-mediated redox reaction, e.g. compounds which are substrates of a NAD(H)-dependent oxidoreductase. Suitable analytes are triglyceride, ascorbinic acid, glucose, glucose-6-phosphate, cholesterol, glycerol, glycerol phosphate, lactate, ketones like 3-hydroxy butyrate, L-amino acids, like glutamate or cysteine, glutathione, peptides, urea, ammonium, salicylate, pyruvate, $CO_2$, malate, ethanol, formaldehyde and sorbitol.

In a yet further embodiment, the analyte is selected from the group consisting of glucose, glucose-6-phosphate, cholesterol, glycerol, glycerol phosphate, lactate, ketones like 3-hydroxy butyrate, L-amino acids, like glutamate, malate, ethanol, formaldehyde and sorbitol, more preferably glucose.

As completely obvious to the skilled artisan the method of the invention implies that the step of reacting the analyte with the reagent system is performed by using a light source capable of inducing fluorescence in the coenzyme. In the presence of such light a fluorescent signal is generated that reflects the change in the co-enzyme's redox status, correlates with the concentration of the analyte of interest and can be measured.

Thus, as the invention also relates to a method for determining the concentration and/or amount of an analyte in a sample comprising following steps:
 (a) mixing an NAD(H)-dependent oxidoreductase and an oxidized form of the fluorogenic coenzyme with the sample, thereby
 (b) reacting the analyte with the reagent system comprising an NAD(H)-dependent oxidoreductase and the oxidized form of the fluorogenic coenzyme,
 (c) measuring the fluorescence emission of the reduced coenzyme,
 (d) determining the amount and/or concentration of the analyte based on the fluorescence emission of the fluorogenic coenzyme, wherein said fluorogenic coenzyme is a compound of the invention.

In another embodiment the kit and/or reagent system compromises a third fluorophore which is used as an internal fluorescence standard, whereas in order to avoid spectral crosstalk this third fluorophore has a higher emission wavelength separated from the second fluorophore by a minimum of about 100 nm, preferable more than about 140 nm In order be compatible with LED excitation sources, it is preferred that the emission wavelength of the third fluorophore is between about 660 and about 900 nm.

In a further preferred embodiment, the third fluorophore is used in the methods of the invention, in particular as internal fluorescence standard.

The NAD(H)dependent-oxidoreductase used for determining the analyte of interest usually is provided in a solution, which is preferably buffered, or as dry substance.

Preferably, an enzyme is best used in a certain range of buffer conditions. The reagent system or kit of the invention thus will usually comprise the NAD(H)-dependent oxidoreductase, the compound of the invention and a buffer system allowing for enzymatic reaction of the oxidoreductase with the analyte of interest. The skilled artisan will have no problem at all to select such buffer conditions since those are broadly known in the art.

The reagent system or kit can be provided in a ready to use form and mixed with the sample to be analyzed or it can be generated by mixing the individual reagents, in particular the NAD(H)dependent-oxidoreductase and the compound of the invention, and optionally buffer and/or reagents and/or third fluorophore where required, with the sample in any desired order.

A large number of oxidoreductase or dehydrogenase enzymes use NAD(P) as a coenzyme. All these enzymes are "NAD(H)-dependent oxidoreductases" in the sense of the present invention.

"NAD(P)" is meant to encompass NAD and NADP.

Enzymes can be classified based on Enzyme Commission (EC) nomenclature recommended by the Nomenclature Committee of the International Union of Biochemistry and Molecular Biology (IUBMB) (see, for example, www.expasy.ch/sprot/enzyme.-html).

Oxidoreductase enzymes utilize NADH or NADPH as cofactors. For example, oxidoreductases are classified as oxidoreductases acting on the CH-OH group of donors with NADH or NADPH as an acceptor (EC 1.1.1); oxidoreductases acting on the aldehyde or oxo group of donors with NADH or NADPH as an acceptor (EC 1.2.1); oxidoreductases acting on the CH-CH group of donors with NADH or NADPH as an acceptor (EC 1.3.1); oxidoreductases acting on the CH—NH2 group of donors with NADH or NADPH as an acceptor (EC 1.4.1); oxidoreductases acting on the CH—NH group of donors with NADH or NADPH as an acceptor (EC 1.5.1); oxidoreductases acting on NADH or NADPH (EC 1.6); and oxidoreductases acting on NADH or NADPH with NADH or NADPH as an acceptor (EC 1.6.1).

Additional oxidoreductases include oxidoreductases acting on a sulfur group of donors with NADH or NADPH as an acceptor (EC 1.8.1); oxidoreductases acting on diphenols and related substances as donors with NADH or NADPH as an acceptor (EC 1.10.1); oxidoreductases acting on hydrogen as donor with NADH or NADPH as an acceptor (EC 1.12.1); oxidoreductases acting on paired donors with incorporation of molecular oxygen with NADH or NADPH as one donor and incorporation of two atoms (EC 1.14.12) and with NADH or NADPH as one donor and incorporation of one atom (EC 1.14.13); oxidoreductases oxidizing metal ions with NADH or NADPH as an acceptor (EC 1.16.1); oxidoreductases acting on —CH2 groups with NADH or NADPH as an acceptor (EC 1.17.1); and oxidoreductases acting on reduced ferredoxin as donor, with NADH or NADPH as an acceptor (EC 1.18.1).

Exemplary oxidoreductases for use as part of a reagent system in a method according to the present invention include adenosylhomocysteine hydrolase, L-alanine dehydrogenase, alcohol dehydrogenase (ADH), aldose reductase (AR), catalase, 1-deoxy-D-xylulose 5-phosphate reductoisomerase (DOXPR), dihydrodipicolinate reductase (DHPR), dihydrofolate reductase (DHFR), 3-isopropylmalate (IPMDH), enoyl ACP reductase (EACPR), formate dehydrogenase, glyceraldehyde-3-phosphate dehydrogenase (GAPDH), D2-hydroxyisocaproate dehydrogenase, 3-hydroxy-3-methylglutaryl coenzyme A reductase (HMG CoAR), inosine monophosphate dehydrogenase (IMPDH), lactate dehydrogenase (LDH), malate dehydrogenase, glutamic dehydrogenase, glucose dehydrogenase, P450 reductase, D3-phosphoglycerate dehydrogenase, shikimate dehydrogenase, tetrahydrofolate reductase, trypanothione reductase, steroid dehydrogenases, cholesterin dehydrogenase, and dihydrosterol dehydrogenase (E.C. 1.1.1.145).

In one embodiment the oxidoreductase used as part of a reagents system in a method according to the present invention is preferably selected from the group comprising glucose dehydrogenase (E.C.1.1.1.47), lactate dehydrogenase (E.C.1.1.1.27, 1.1.1.28), malate dehydrogenase (E.C.1.1.1.37), glycerin dehydrogenase (E.C.1.1.1.6), alcohol dehydrogenase (E.C.1.1.1.1), amino acid dehydrogenase, e.g., L-amino acid dehydrogenase (E.C.1.4.1.5), cholesterin dehydrogenase, and dihydrosterol dehydrogenase (E.C. 1.1.1.145).

The invention is to be explained in more detail by the following figures and examples.

"about" in the context of a wavelength has the meaning of +/−10 nm, preferably +/−5 nm.

EXAMPLES

Example 1

Synthesis of
N6-[N-(6-aminohexyl)carbamoylmethyl] carbaNAD
and N6-[N-(6-aminohexyl)carbamoylmethyl]
carbaNADH For the synthesis of N6-[N-(6-aminohexyl)carbamoylmethyl] carbaNADH a similar procedure as described in Lindberg, M.; Larsson, Per O.; Mosbach, K. European Journal of Biochemistry (1973), 40(1), 187-93 was used:
1.1 Synthesis of N6 carboxymethyl CarbaNAD Therefore 2 g (3 mmol) carbaNAD synthesized as described in WO 2011/012270 and 2 g (10.7 mmol) iodacetic acid were dissolved in 25 ml water; pH was adjusted to 6.5 with ~13 ml 2 M lithium hydroxide. The reaction mixture was stored at room temperature for 7 days. The pH was adjusted every day with 2 M lithium hydroxide to pH 6.5. Then the pH of the aqueous solution was adjusted to pH 11.3 with 0.5 M sodium hydroxide and heated for 1 h to 75° C. After adjusting the pH with 1 M HCl to pH 7, the mixture was given to ice cold acetone (250 ml acetone for 25 ml mixture) and the resulting suspension was stored overnight at 4° C. The supernatant was removed by decantation. The remainder was dissolved in 15 ml water and purified by IEX chromatography on DEAE Sephadex A25 column, d=1.6 cm h=25 cm) applying a gradient from eluent A (deionized water) to 2 M ammonium acetate within 4 h. Fractions were monitored by using LC-MS and fractions containing the right substance (719 Da) were collected. The solvent was removed the remainder, dissolved in pure water and lyophilized. (yield N6 carboxy methyl carbaNAD: 75 mg)

1.2 Synthesis of N6-[N-(6-aminohexyl)carbamoylmethyl] carbaNAD

To a solution of 72 mg (0.1 mmol) N6 carboxy methyl carbaNAD in 5 ml 1 M (5 mmol) hexamethylendiamine, 300 mg (0.7 mmol) 1-Cyclohexyl-3-(2-morpholinoethyl)-carbodiimine metho p toluene sulfonate were added in portions at room temperature. Within 3 h, the pH was adjusted to pH 4.7 with 0.5 M HCl and the mixture was stirred at room temperature for 20 h. The mixture was directly applied on a RP18 Hypersil column (5 μm, 21×250 mm) chromatography applying a gradient: 100% eluent A, in 60 min to 100% eluent B, flow 9 ml/min with eluent A being 0.1 M Triethylammonium acetate (pH 7) and eluent B (being a mixture of 0.2 l A with 0.8 l acetonitrile). Fractions were monitored by using LC-MS and fractions containing the right substance (818 Da) were collected.

1.3 Synthesis of N6-[N-(6-"Cy 3" aminohexyl)carbamoylmethyl] carbaNAD

A solution of 1.6 mg Cy3 NHS ester (2-[3-(1,3-dihydro-1,3,3-trimethyl-5-sulfo-2H-indol-2-ylidene)-1-propen-1-yl]-1-[6-[(2,5-dioxo-1-pyrrolidinypoxy]-6-oxohexyl]-3,3-dimethyl-5-sulfo-3H-Indolium inner salt from GE Healthcare) in 100 μl acetonitrile was added at room temperature to a solution of 3 mg N6-[N-(6-aminohexyl)carbamoylmethyl] carbaNAD in 0.6 ml Borate buffer pH 8.5. The mixture was stirred overnight and the evaporated to dryness under vacuum by using a rotary evaporator. The remainder was dissolved in 1.2 ml 0.1 M Triethylammonium acetate (pH 7) and purified by using an X Bridge L18 column (5 μm, 10×250 mm) Eluent A was 0.1 M Triethylammonium acetate (pH7) and eluent B was acetonitrile. The following gradient was applied: 5 min 5% B and within 5 min to 50% B, flow 4 ml/min. Fractions were monitored by using LC-MS and fractions containing the right substance (1433 Da) were collected.

Example 2

Reduction to N6-[N-(6-"Cy 3" aminohexyl)carbamoylmethyl] carbaNADH

N6-[N-(6-"Cy 3" aminohexyl)carbamoylmethyl] carbaNADH was generated in situ from N6-[N-(6-"Cy 3" aminohexyl)carbamoylmethyl] carbaNAD by an enzymatic reaction with glucose and a Glucose dehydrogenase (as described in WO 2010/094632).

Figure 1:
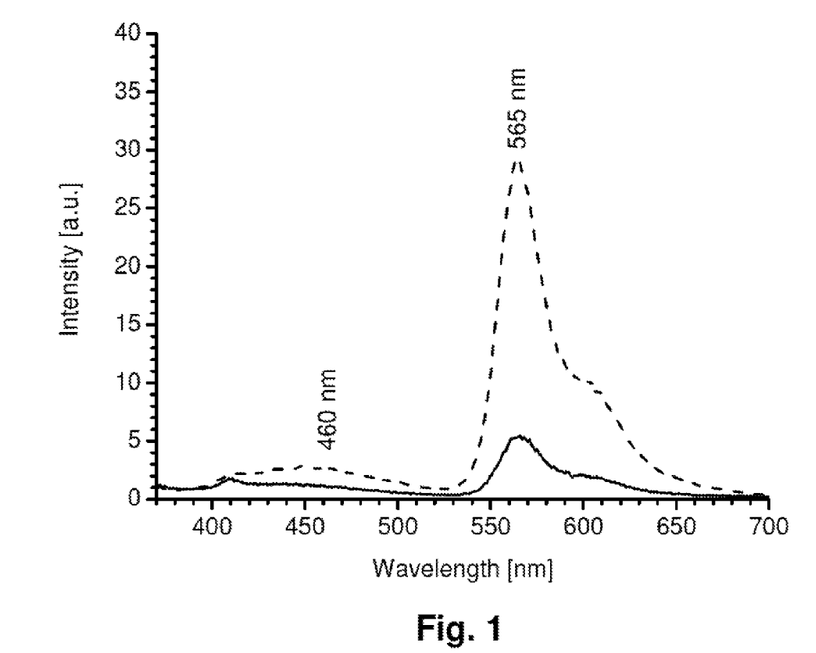
FIG. 1 shows the fluorescence emission spectra of the reaction mixture of the enzymatic reduction of N6-[N-(6-"Cy 3"-aminohexyl) carbamoylmethyl] carbaNAD to N6-[N-(6-"Cy 3" aminohexyl) carbamoylmethyl] carbaNADH before reaction start (full line) and completion of the reaction (dotted line). The spectra were recorded from 370 nm to 700 nm with an excitation wavelength of 360 nm.

The reaction was carried out in a total volume of 1.5 ml in a closed vial in 0.1 M Potassium phosphate buffer pH 7.0 at 25° C. with 200 mM Sodium Chloride, 100 mM Glucose, 1 mM N6-[N-(6-"Cy 3" aminohexyl)carbamoylmethyl] carbaNAD and 4 μM Glucose dehydrogenase. The fluorescence spectra from 370 nM to 700 nM were recorded with an excitation wavelength of 360 nM directly before reaction start and after completion of the reaction (see FIG. 1). The generated N6-[N-(6-Cy3 aminohexyl) carbamoylmethyl] carbaNADH can be detected by the formation of two peaks at about 460 nm and 565 nm. The peak at about 460 nm represents the fluorescence of carbaNADH itself (see Ketteler et al., Fluorescence Properties of Carba Nicotinamide Adenine Dinucleotide for Glucose Sensing, ChemPhysChem (2012), 13(5), 1302-1306), whereas the peak at 565 nm represents the result of FRET to Cy3.

The invention claimed is:

1. A compound comprising
   (1) the oxidized form of a carbaNADH-based first fluorophore, and
   (2) a second fluorophore that is excitable with light having a wave-length of between 445 to 540 nm, and that has an emission maximum of greater than 560 nm,
   wherein the carbaNADH-based first fluorophore and the second fluorophore are covalently linked and the second fluorophore comprises, as a core, a chromophore selected from the group consisting of a 2-[3-(1,3-dihydro-1,3,3-trimethyl-2H-indol-2-ylidene)-1-propen-1-yl]-1,3,3-trimethyl-3H-indolium chromophor moiety, a 5,6-dichloro-2-[3-(5,6-dichloro-1,3-dihydro-1,3-dimethyl-2H-benzimidazol-2-ylidene)-1-propen-1-yl]-1,3-dimethyl1H-benzimidazolium chromophor moiety, a 1-methyl-4-[3-(1-methyl-4(1H)-quinolinylidene-1-propen-1-yl]-quinolinium chromophore moiety, and a 2-(4-(Diethylamino)-2-hydroxyphenyl)-4-(4-(diethyliminio)-2-hydroxycyclohexa-2,5-dienylidene)-3-oxocyclobut-1-enolate chromophore moiety.

2. The compound of claim 1, wherein
   (a) the distance between the first and the second fluorophore is between 1.5 and 5 nm,
   and/or
   (b) the compound consists of
      (i) the oxidized form of a carbaNADH-based first fluorophore, and
      (ii) a second fluorophore that is excitable with light having a wave-length of between 445 to 540 nm, and that has an emission maximum of greater than 560 nm, and
      (iii) a linker molecule with a length of 25 atoms or less,
   and/or
   (c) wherein the oxidized form of the first fluorophore is carbaNAD
   and/or
   (d) the oxidized form of the carbaNADH-based first fluorophore is a carbaNADH-based first fluorophore of formula II (II)

wherein

Q is a NR$_1$R$_2$, wherein R$_1$ and R$_2$ are independently selected from H, a C$_1$ to C$_{12}$ alkyl group, a C$_1$ to C$_{12}$ alkenyl group and a C$_1$ to C$_{12}$ alkinyl group, optionally wherein one or more carbon atoms of the alkyl group, a alkenyl group and a alkinyl group is substituted with O, N or S and/or optionally wherein said C$_1$ to C$_{12}$ alkyl, alkenyl or alkinyl group is substituted with =O, —OH, —SH, =S or a C$_1$ to C$_4$ alkyl, wherein optionally one or more carbon atoms of the alkyl group is substituted with O, N or S, and J is selected from H, a C$_1$ to C$_{12}$ alkyl group, a C$_1$ to C$_{12}$ alkenyl group and a C$_1$ to C$_{12}$ alkinyl group, optionally wherein one or more carbon atoms of the alkyl group, a alkenyl group and a alkinyl group is substituted with O, N or S and/or optionally wherein said C$_1$ to C$_{12}$ alkyl, alkenyl or alkinyl group is substituted with =O, —OH, —SH, =S or a C$_1$ to C$_4$ alkyl, wherein optionally one or more carbon atoms of the alkyl group is substituted with O, N or S, particularly wherein one of J and Q is connected via a linker molecule with a length of 25 atoms or less to the second fluorophore, and T is a hydrogen atom or phosphate group, especially wherein Q is substituted with N-(6"cy3" aminohexyl)carbomyolmethyl.

3. The compound of claim 1, wherein the second fluorophore comprises a "Cy3" (=2-[3-(1,3-dihydro-1,3,3-trimethyl-2H-indol-2-ylidene)-1-propen-1-yl]-1,3,3-trimethyl-3H-indolium) moiety.

4. A compound of claim 1, selected from the group consisting of
(i) N6-[N-(6-"Cy 3" aminohexyl)carbamoylmethyl] carbaNADH, or
(ii) N6-[N-(6-"Cy 3" aminohexyl)carbamoylmethyl] carbaNAD, or
(iii) a mixture of N6-[N-(6-"Cy 3" aminohexyl)carbamoylmethyl] carbaNADH and N6-[N-(6-"Cy 3" aminohexyl)carbamoylmethyl] carbaNAD.

5. A compound comprising
(1) the reduced form of a carbaNADH-based first fluorophore, and
(2) a second fluorophore that is excitable with light having a wave-length of between 445 to 540 nm, and that has an emission maximum of greater than 560 nm, wherein the carbaNADH-based first fluorophore and the second fluorophore are covalently linked and the second fluorophore comprises, as a core, a chromophore selected from the group consisting of a 2-[3-(1,3-dihydro-1,3,3-trimethyl-2H-indol-2-ylidene)-1-propen-1-yl]-1,3,3-trimethyl-3H-indolium chromophor moiety, a 5,6-dichloro-2-[3-(5,6-dichloro-1,3-dihydro-1,3-dimethyl-2H-benzimidazol -2-ylidene)-1-propen-1-yl]-1,3-dimethyl1H-benzimidazolium chromophor moiety, a 1-methyl-4-[3-(1-methyl-4(1H)-quinolinylidene-1-propen-1-yl]-quinolinium chromophore moiety, and a 2-(4-(Diethylamino)-2-hydroxyphenyl)-4-(4-(diethyliminio)-2-hydroxycyclohexa-2,5-dienylidene)-3-oxocyclobut-1-enolate chromophore moiety.

6. The compound of claim 5, wherein
(a) the distance between the first and the second fluorophore is between 1.5 and 5 nm, and/or
(b) the compound consists of
  (i) the reduced form of a carbaNADH-based first fluorophore, and
  (ii) a second fluorophore that is excitable with light having a wave-length of between 445 to 540 nm, and that has an emission maximum of greater than 560 nm, and
  (iii) a linker molecule with a length of 25 atoms or less, and/or
(c) wherein the reduced form of the first fluorophore is carbaNADH.
(d) the reduced form of the carba a carbaNADH-based first fluorophore is a carbaNADH-based first fluorophore of formula III (III)

wherein

Q is a NR$_1$R$_2$, wherein R$_1$ and R$_2$ are independently selected from H, a C$_1$ to C$_{12}$ alkyl group, a C$_1$ to C$_{12}$ alkenyl group and a C$_1$ to C$_{12}$ alkinyl group, optionally wherein one or more carbon atoms of the alkyl group, a alkenyl group and a alkinyl group is substituted with O, N or S and/or optionally wherein said C$_1$ to C$_{12}$ alkyl, alkenyl or alkinyl group is substituted with =O, —OH, —SH, =S or a C$_1$ to C$_4$ alkyl, wherein optionally one or more carbon atoms of the alkyl group is substituted with O, N or S, and J is selected from H, a C$_1$ to C$_{12}$ alkyl group, a C$_1$ to C$_{12}$ alkenyl group and a C$_1$ to C$_{12}$ alkinyl group, optionally wherein one or more carbon atoms of the alkyl group, a alkenyl group and a alkinyl group is substituted with O, N or S and/or optionally wherein said C$_1$ to C$_{12}$ alkyl, alkenyl or alkinyl group is substituted with =O, —OH, —SH, =S or a C$_1$ to C$_4$ alkyl, wherein optionally one or more carbon atoms of the alkyl group is substituted with O, N or S, particularly wherein one of J and Q is connected via a linker molecule with a length of 25 atoms or less to the second fluorophore, and T is a hydrogen atom or phosphate group, especially wherein Q is substituted with N-(6"cy3" aminohexyl)carbomyolmethyl.

7. A method for determining an analyte in a sample using an NAD(H)-dependent oxidoreductase and the oxidized form of a fluorogenic coenzyme, the method comprising following steps:
   (a) mixing an NAD(H)-dependent oxidoreductase and the oxidized form of the fluorogenic coenzyme of claim 1 with the sample, thereby
   (b) reacting the analyte with the reagent system comprising an NAD(H)-dependent oxidoreductase and the oxidized form of the fluorogenic coenzyme of claim 1,
   (c) measuring the fluorescence emission of the reduced coenzyme.

8. The method according to claim 7, wherein
   (a) a change in the oxidized form of the fluorogenic coenzyme is generated in step (b) of claim 7
      (i) wherein said change in the oxidized form of the fluorogenic coenzyme is an reduction, and/or
      (ii) wherein said change in the coenzyme correlates with the amount and/or concentration of the analyte, and/or
   (b) wherein the method of claim 7 is followed by determining the amount and/or concentration of the analyte based on the fluorescence emission of the fluorogenic coenzyme.

9. The method according to claim 7,
   (a) wherein the analyte is selected from the group consisting of glucose, glucose-6-phosphate, cholesterol, glycerol, glycerol phosphate, lactate, ketones like 3-hydroxy butyrate, L-amino acids, like glutamate, malate, ethanol, formaldehyde and sorbitol, more preferably glucose, and/or
   (b) wherein a third fluorophore is used as internal fluorescence standard, and wherein the emission wavelength of said third fluorophore is separated from the emission wavelength of the second fluorophore by a minimum of 100 nm, preferably by more than 140 nm, more preferably wherein the emission wavelength of said third fluorophore is between 660 and 900 nm.

* * * * *